(12) United States Patent
Jan et al.

(10) Patent No.: US 8,702,971 B2
(45) Date of Patent: Apr. 22, 2014

(54) PROCESS AND APPARATUS FOR ALKYLATING AND HYDROGENATING A LIGHT CYCLE OIL

(75) Inventors: Deng-Yang Jan, Elk Grove Village, IL (US); Vasant P. Thakkar, Elk Grove Village, IL (US); Christopher P. Nicholas, Evanston, IL (US)

(73) Assignee: UOP LLC, Des Plaines, IL (US)

( * ) Notice: Subject to any disclaimer, the term of this patent is extended or adjusted under 35 U.S.C. 154(b) by 855 days.

(21) Appl. No.: 12/752,026

(22) Filed: Mar. 31, 2010

(65) Prior Publication Data

US 2011/0240519 A1   Oct. 6, 2011

(51) Int. Cl.
*C10G 35/00*   (2006.01)
(52) U.S. Cl.
USPC .......................................................... 208/133
(58) Field of Classification Search
USPC ................. 208/70, 69, 46, 133; 422/608, 619
See application file for complete search history.

(56) References Cited

U.S. PATENT DOCUMENTS

| | | | |
|---|---|---|---|
| 3,470,084 A | 9/1969 | Scott | |
| 3,574,720 A * | 4/1971 | De Vault | 562/33 |
| 3,907,663 A * | 9/1975 | Owen | 208/70 |
| 4,090,948 A | 5/1978 | Schwarzenbek | |
| 4,447,312 A * | 5/1984 | Angevine et al. | 208/46 |
| 4,871,444 A | 10/1989 | Chen et al. | |
| 4,990,239 A | 2/1991 | Derr, Jr. et al. | |
| 5,154,818 A | 10/1992 | Harandi et al. | |
| 5,171,916 A | 12/1992 | Le et al. | |
| 5,219,814 A | 6/1993 | Kirker et al. | |
| 5,599,441 A | 2/1997 | Collins et al. | |
| 5,900,520 A | 5/1999 | Mazzone et al. | |
| 7,247,233 B1 | 7/2007 | Hedrick et al. | |
| 7,312,370 B2 | 12/2007 | Pittman et al. | |
| 8,231,847 B2 * | 7/2012 | da Silva Ferreira Alves et al. | 422/608 |
| 2003/0111385 A1 | 6/2003 | Cash et al. | |
| 2009/0045099 A1 | 2/2009 | Yung et al. | |
| 2009/0159489 A1 | 6/2009 | Lopez et al. | |
| 2010/0012552 A1 | 1/2010 | James, Jr. et al. | |
| 2011/0201858 A1* | 8/2011 | Hwang et al. | 585/314 |

FOREIGN PATENT DOCUMENTS

| | | |
|---|---|---|
| EP | 1 201 730 A1 | 5/2002 |
| RU | 2 144 942 C1 | 1/2000 |
| WO | 0039253 | 7/2000 |

OTHER PUBLICATIONS

Tseneji Sano, Hiroyuki Hawiwara, Kiyomi Okabe, Hideo Okado, Kenji Saito and Haruo Takaya ; "Olefin Hydrogenation over Zeolite H-ZSM-5"; Sekiyu Gakkashi ; 29 No. 1. 1986 ; p. 89.*
Bouchy et al., "Hydrogenation and Hydrocracking of a Model Light Cycle Oil Feed. 1. Properties of a Sulfided NiMo Hydrotreating Catalyst", "Industrial & Engineering Chemistry Research", vol. 31, No. 12, Dec. 1992, pp. 2661-2669.
"H P Innovations: Upgrade Light Cycle Oil to Diesel", "Hydrocarbon Processing", vol. 80, No. 5, May 2001, p. 30.

(Continued)

*Primary Examiner* — Randy Boyer
*Assistant Examiner* — Juan Valencia
(74) *Attorney, Agent, or Firm* — James C Paschall

(57) ABSTRACT

One exemplary embodiment can be a process for alkylating and hydrogenating a light cycle oil. The process can include passing the light cycle oil, one or more C2-C6 alkenes, and hydrogen through a reaction vessel containing an alkylation zone and a hydrogenation zone. Generally, the hydrogen is at least partially comprised from a hydrocarbon product stream from a fluid catalytic cracking zone.

7 Claims, 2 Drawing Sheets

(56) References Cited

OTHER PUBLICATIONS

Tailleur, "Diesel Upgrading into a Low Emissions Fuel", "Fuel Processing Technology", vol. 87, No. 9, 2006, pp. 759-767.

Vaarkamp et al., "Upgrading FCC Light Cycle Oil to Diesel Using the Engelhard—Washington Redar Process", "King Fand University of Petroleum and Minerals Research Institute Annual Catalysts in Petroleum Refining and Petrochemicals Symposium Papers 2001", 2001, pp. 18.

* cited by examiner

PROCESS AND APPARATUS FOR ALKYLATING AND HYDROGENATING A LIGHT CYCLE OIL

FIELD OF THE INVENTION

This invention generally relates to a process and apparatus for alkylating and hydrogenating a light cycle oil.

DESCRIPTION OF THE RELATED ART

Generally, some of the demand for transportation fuel has been shifting toward a middle distillate, such as diesel fuel. A light cycle oil (hereinafter may be abbreviated "LCO") can have a boiling point range that may fall within the diesel range. The LCO is typically blended into the diesel pool. However, the quantity of blended LCO may be limited because the typical level of contaminates in the LCO can be high and the cetane number may be low, making LCO undesirable as a diesel fuel. One approach to upgrading LCO may include hydrotreating. Unfortunately, although this approach can reduce sulfur amounts to meet specifications, a significant amount of hydrogen may be required. In many refineries, hydrogen may be in a limited supply and can be a relatively valuable commodity.

Another approach may be subjecting the LCO to hydrotreating followed by selective ring opening. The hydrogen consumption may be even higher than for deep hydrotreating, and significant amounts of gasoline may be produced along with the desired diesel fraction. Gasoline may be co-produced because the activation energy for the ring opening may be greater than for the dealkylation or side chain cracking. Therefore, it is difficult to open the aromatic rings without dealkylating the side chains. However, refineries may have significant amounts of light alkenes, e.g., C2-C6 alkenes, generated by units such as fluid catalytic cracking. Generally, it would be beneficial to convert C2-C6 olefins to a middle distillate fuel product, such as diesel, instead of gasoline in some instances. At a minimum, it would be advantageous to provide the refinery the flexibility to manufacture a desired fuel to meet the current demand.

SUMMARY OF THE INVENTION

One exemplary embodiment can be a process for alkylating and hydrogenating a light cycle oil. The process can include passing the light cycle oil, one or more C2-C6 alkenes, and hydrogen through a reaction vessel containing an alkylation zone and a hydrogenation zone. Generally, the hydrogen is at least partially comprised from a hydrocarbon product stream from a fluid catalytic cracking zone.

Another exemplary embodiment may be a process for alkylating and hydrogenating a light cycle oil. The process can include passing the light cycle oil, one or more C2-C6 alkenes, and hydrogen upwards through a reaction vessel containing a reaction zone for alkylating and hydrogenating the light cycle oil, and sending a catalyst from the reaction zone to a regeneration zone in a catalytic cracking zone.

Yet another exemplary embodiment can be an apparatus that may include a catalytic cracking zone, a fractionation zone, a separation zone, a treatment zone, and a reaction vessel. The catalytic cracking zone may produce a hydrocarbon product stream. Typically, the fractionation zone receives the hydrocarbon product stream and provides a light naphtha stream and a light cycle oil stream. The separation zone may separate a stream including hydrogen and ethene from the light naphtha stream. Generally, the treatment zone is adapted to receive the stream including hydrogen and ethene, and may include a first removal zone for removing hydrogen sulfide, and a washing zone for removing ammonia. Usually, the reaction vessel is provided for alkylating and hydrogenating the light cycle oil stream. The reaction vessel may receive a feed including hydrogen and one or more C2-C6 alkenes, and the light cycle oil stream. The light cycle oil and hydrogen may be obtained from the hydrocarbon product stream.

The embodiments disclosed herein can provide a process and an apparatus for upgrading an LCO for utilization as a middle distillate fuel product, such as diesel fuel. Particularly, the embodiments herein provide a process for increasing the cetane number of an LCO. As such, the embodiments provided herein can allow utilization of light alkenes ranging from C2-C6 to alkylate aromatics. As a result, the 2-ring and 3-ring aromatics that may be present in the LCO can be upgraded to allow blending of the treated LCO in various diesel tankage in the refinery. Thus, the embodiments disclosed herein can provide flexibility in shifting fuel production from gasoline to diesel fuel or vice-versa. Furthermore, components in a fluid catalytic cracking off-gas may also be utilized in the process and be upgraded from typical use, such as fuel gas. The hydrogen containing stream, often referred to as an FCC dry-gas that may contain up to about 15%, typically about 10-about 15%, by volume, hydrogen, can be used for saturating aromatics as well as removing other impurities by processes such as hydrodesulfurizing and hydrodenitrogenating. In addition, any ethene in the FCC dry-gas may also be used for alkylating one or more aromatics in the LCO. As a consequence, the quality of the product, such as diesel fuel, can be further improved. By coupling aromatic alkylation with hydrotreating, the refinery can potentially produce middle distillate fuels, such as diesel fuels, by meeting sulfur and cetane number specifications and utilizing light alkenes.

DEFINITIONS

As used herein, the term "stream" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 . . . Cn where "n" represents the number of carbon atoms in the one or more hydrocarbon molecules. Furthermore, a superscript "+" or "−" may be used with an abbreviated one or more hydrocarbons notation, e.g., $C3^+$ or $C3^-$, which is inclusive of the abbreviated one or more hydrocarbons. As an example, the abbreviation "$C3^+$" means one or more hydrocarbon molecules of three carbon atoms and/or more. Typically, a stream can include at least one of hydrogen, one or more alkenes, a light naphtha, a heavy naphtha, a light cycle oil, a heavy cycle oil, and a heavy slurry oil.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "rich" can mean a stream exiting a vessel that may have a concentration of one or more compounds exceeding a stream entering the vessel.

As used herein, the term "lean" can mean a stream exiting a vessel that may have a concentration of one or more compounds less than a stream entering the vessel.

As used herein, the term "dilute" can mean no more than about 50%, by volume, of an individual compound, such as hydrogen, in a stream.

As used herein, the term "substantially" can mean an amount of at least generally about 80%, preferably about 90%, and optimally about 99%, by mole, of a compound or class of compounds in a stream.

As used herein, the term "cetane number" can mean a diesel fuel rating comparable to the octane-number rating for gasoline. Typically, it is the percentage of cetane ($C_{16}H_{34}$) that is mixed with heptamethylnonane to give the same ignition performance under standard conditions as the fuel in question. The derived cetane number for a diesel fuel can be determined by ASTM D6890-09.

As used herein, the term "gasoline" may be a mixture of volatile hydrocarbons suitable for use in a spark-ignited internal combustion engine and having an octane number of at least 60. The major components can include branch and straight chain paraffins, cyclic paraffins, and aromatics. The standard specifications for gasoline can be determined by ASTM D4814-09b.

As used herein, the term "light naphtha" can be a fraction boiling up to about 90° C. and can include up to 6 carbon atom molecules and other gases. As an example, a light naphtha can include one or more of methane, ethane, ethene, propane, propene, butane, butene, pentane, pentene, hexane, hexene, hydrogen, hydrogen sulfide, carbon monoxide, and nitrogen. Typically, a light naphtha can include gasoline, one or more C1-C5 hydrocarbons, and hydrogen.

As used herein, the term "heavy naphtha" can be a fraction boiling from about 90-about 200° C. and include one or more molecules of 6-12 carbon atoms.

As used herein, the term "light cycle oil" may be a cycle oil from catalytic cracking that can be used as a feed in hydrocracking and typically has a boiling point in the range of about 205-about 400° C. Typically, the light cycle oil can contain about 8-about 20 carbon atoms per molecule.

As used herein, "heavy cycle oil" can include compounds having about 20-about 70 carbon atoms per molecule. A heavy cycle oil may substantially include components boiling in the range of about 340-about 570° C.

As used herein, the terms "alkene" and "olefin" may be used interchangeably.

As used herein, the term "communication" can mean that material flow is operatively permitted, directly or indirectly, between enumerated components.

As used herein, the term "overhead stream" can mean a stream, typically including one or more gases, which may be removed at or proximate to a top of a vessel.

As used herein, the term "bottom stream" can mean a stream, typically including one or more liquids, which may be removed at or proximate to a bottom of a vessel.

As used herein, the terms "absorption" and "adsorption" may include processes such as, respectively, adsorption and absorption.

As used herein, the term "zeolite" can refer to a topological structure of a molecular sieve as described by Atlas of Zeolite-Framework Types maintained by the International Zeolite Association Structure Commission.

As used herein, the term "FAU zeolite" can include any zeolite of the FAU structure such as zeolite X or zeolite Y.

DETAILED DESCRIPTION

Figure 1:
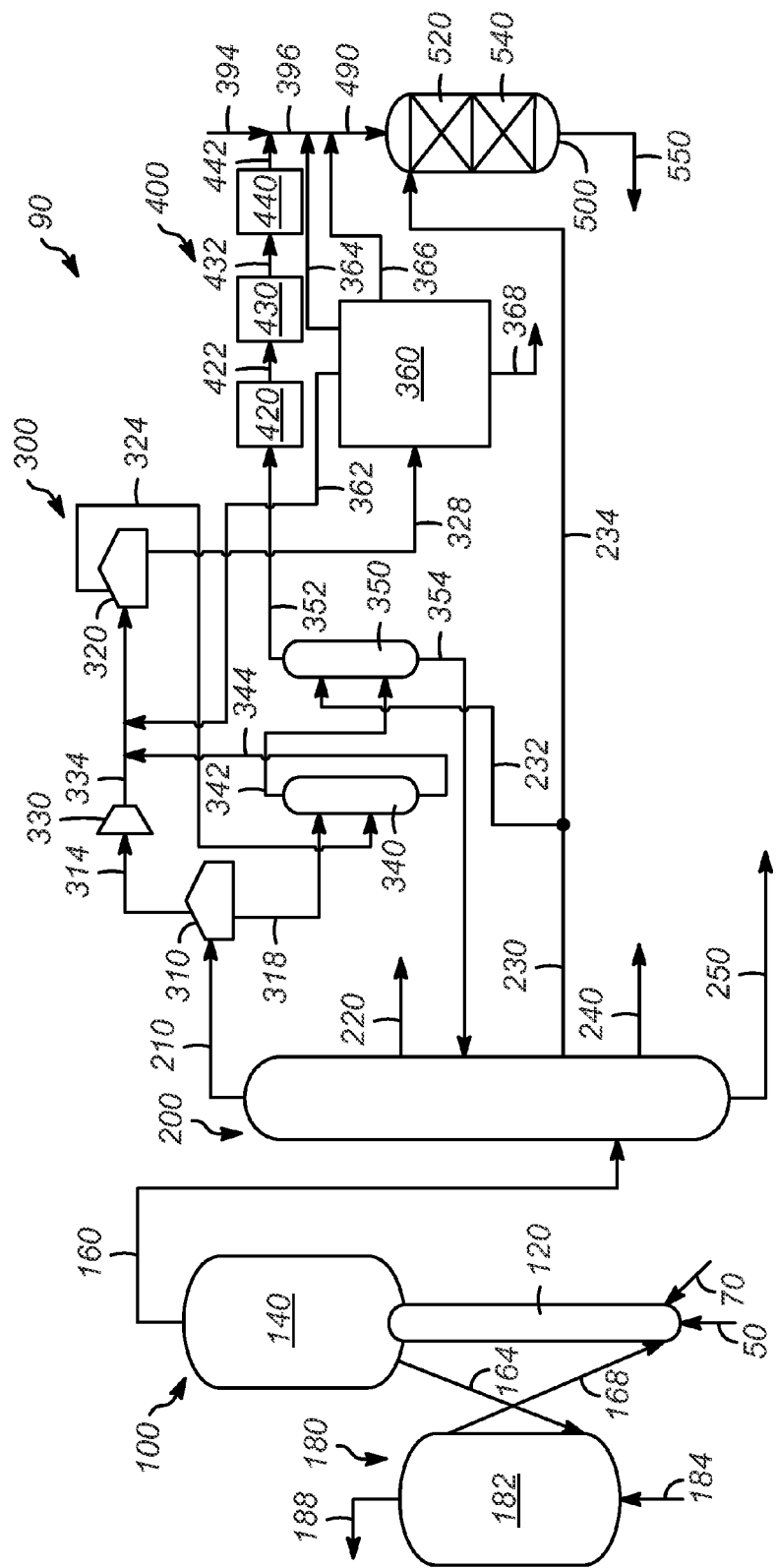
FIG. 1 is a schematic depiction of an exemplary apparatus for alkylating and hydrogenating an LCO.

Referring to FIG. 1, an apparatus 90 for alkylating and hydrogenating an LCO can include a catalytic cracking zone 100, a fractionation zone 200, a separation zone 300, a treatment zone 400, and a reaction vessel 500. It should be noted that process flow lines in the figures can be referred to as, e.g., lines, portions, gases, feeds, products, or streams. Particularly, a line can contain one or more portions, gases, feeds, products, or streams, and one or more portions, gases, feeds, products, or streams can be contained by a line.

The catalytic cracking zone 100 can include a riser 120 or riser reactor 120, a reactor 140, and a regeneration zone 180. The riser 120 can receive a fluidizing gas 50 and a catalytic cracking feed 70. Generally, the catalytic cracking zone 100 is preferably a fluid catalytic cracking (may be abbreviated herein as "FCC") zone 100. Although the reactor 140 can include a fixed bed, a moving bed, or a fluidized bed, preferably the reactor 140 is a fluidized bed.

Generally, the reactor 140 can communicate with the riser 120. The riser 120 can receive a feed 70 that can have a boiling point of about 180-about 800° C. Typically, the feed 70 can be at least one of a gas oil, a vacuum gas oil, an atmospheric gas oil, and an atmospheric residue. Alternatively, the feed 70 can be at least one of a heavy cycle oil and a slurry oil. Generally, the feed 70 can be provided at any suitable height on the riser 120, such as above the fluidizing gas 50 including steam and/or a light hydrocarbon. The feed 70 can be provided at a distance sufficient to provide a good dispersion of the up-flow stream containing the feed and/or catalyst, if desired.

The catalyst can be a single catalyst or a mixture of different catalysts. In one exemplary embodiment, the catalyst may include two components or catalysts, namely a first component or catalyst, and optionally a second component or catalyst. Such a catalyst mixture is disclosed in, e.g., U.S. Pat. No. 7,312,370 B2.

Generally, the first component may include any of the well-known catalysts that are used in the art of FCC, such as an active amorphous clay-type catalyst and/or a high activity, crystalline molecular sieve. Zeolites may be used as molecular sieves in FCC processes. Preferably, the first component includes a large pore zeolite, such as a Y-type zeolite, an active alumina material, a binder material, including either silica or alumina, and an inert filler such as kaolin.

Typically, the zeolitic molecular sieves appropriate for the first component have a large average pore size. Usually, molecular sieves with a large pore size have pores with openings of greater than about 0.7 nm in effective diameter defined by greater than about 10, and typically about 12, member rings. Suitable large pore zeolite components may include synthetic and natural zeolites of the FAU and MOR structure types. A portion of the first component, such as the zeolite, can have any suitable amount of a rare-earth metal or rare-earth metal oxide.

The second component if, e.g., a light alkene product is desired, may include a medium or smaller pore zeolite catalyst, such as an MFI, MEL, and/or FER structure types. Preferably, the second component has the medium or smaller pore zeolite dispersed on a matrix including a binder material such as silica or alumina and an inert filler material such as kaolin. The second component may also include some other active material such as a beta zeolite. These compositions may have a crystalline zeolite content of about 10-about 50%, by weight or more, and a matrix material content of about 50-about 90%, by weight. Components containing about 40%, by weight, crystalline zeolite material are preferred, and those with greater crystalline zeolite content may be used. Generally, medium and smaller pore zeolites are characterized by having an effective pore opening diameter of less than or equal to about 0.6 nm, and rings of about 10 or fewer members.

The total catalyst mixture in the reactor 140 may contain about 1-about 25%, by weight, of the second component, namely a medium to small pore crystalline zeolite with greater than or equal to about 1.75%, by weight, of the second component being preferred. When the second component contains about 40%, by weight, crystalline zeolite with the balance being a binder material, an inert filler, such as kaolin, and optionally an active alumina component, the mixture may contain about 4-about 40%, by weight, of the second catalyst with a preferred content of at least about 7%, by weight. The first component may comprise the balance of the catalyst composition.

Generally, the feed 70 in the catalyst mixture can be provided approximate to the bottom of a riser 120. Typically, the riser 120 operates with dilute phase conditions above the point of feed injection with a density that is less than about 320 kg/m$^3$. Generally, the feed 70 may be introduced into the riser 120 by a nozzle. Usually, the feed 70 can have a temperature of about 140-about 300° C. Moreover, additional amounts of feed may be introduced downstream of the initial feed point.

In one exemplary embodiment, heat from the regenerated catalyst gasifies the hydrocarbon feed or oil, and the hydrocarbon feed is thereafter cracked to lighter molecular weight hydrocarbon products in the presence of the catalyst as both are transferred up the riser 120 into the reactor 140. Usually the feed 70 reacts within the riser 120 to form one or more products. The riser 120 can operate at any suitable temperature, and typically operates at a temperature of about 400-about 600° C. at a pressure of no more than about 510 kPa. Typically, side reactions occur in the riser 120 leaving coke deposits on the catalyst that lower catalyst activity. The cracked light hydrocarbon products can thereafter be separated from the coked cracking catalyst using one or more stages of product disengagers and/or cyclones in the reactor 140. Gaseous, cracked products can exit the reactor 140 as a hydrocarbon product stream to a downstream fractionation zone 200, as hereinafter described. The spent or coked catalyst may require regeneration for further use. Coked cracking catalyst, after separation from the gaseous hydrocarbon products and steam stripping to purge any residual hydrocarbon gases, may be carried to the regeneration zone 180 through a spent catalyst line 164.

The regeneration zone 180 can include a regenerator 182, also known as a combustor 182. However, other types of regenerators are suitable. A stream of oxygen-containing gas 184, such as air, may be introduced into the regenerator 182 to contact the coked catalyst. Generally, coke is combusted from the coked catalyst to provide a regenerated catalyst and a flue gas stream 188. However, metals present in the catalytic cracking feed 70 typically are not removed through this combustion regeneration. The catalyst regeneration process can add a substantial amount of heat to the catalyst, providing energy to offset the endothermic cracking reactions occurring in the riser 120. Catalyst and air flow upwardly together within the regenerator 182 and, after regeneration, can be separated by one or more stages of catalyst disengagers and/or cyclones. Regenerated metal-containing catalyst may be carried back to the riser 120 through the regenerated catalyst line 168. Hot flue gas exits the top of the catalyst regenerator 182 as the flue gas stream 188 for further processing. The catalyst regeneration temperature can be about 500-about 900° C., and a pressure of no more than about 510 kPa. As a result of the coke burning, the flue gas stream 188 can contain carbon monoxide, carbon dioxide, nitrogen, and water, along with smaller amounts of other compounds. Exemplary reaction zones and regeneration zones are disclosed in, e.g., U.S. Pat. Nos. 4,090,948; 5,154,818; and 7,312,370 B2.

The one or more products leaving the reactor 140 can exit as the hydrocarbon product stream 160 optionally in a gas phase to the fractionation zone 200. The fractionation zone 200 can include any suitable number of distillation columns, such as one or more distillation columns, and produce a variety of streams or products 210, 220, 230, 240, and 250. Typically, a main column can provide a light naphtha stream 210, a heavy naphtha stream 220, a light cycle oil stream 230, a heavy cycle oil stream 240, and a heavy slurry oil stream 250. Any or all of these may be optionally cooled and pumped back to the main column, typically at a higher location. The light naphtha stream including gasoline and gaseous light hydrocarbons can be cooled to condense heavier components before entering a first receiver 310 of the separation zone 300. Such fractionation zones are disclosed in, e.g., U.S. Pat. No. 3,470,084.

The separation zone 300 can include the first receiver 310, a second receiver 320, a compressor 330, a first absorber 340, a second absorber 350, and another fractionation zone 360. The receiver 310 can provide an overhead stream 314 including one or more gaseous light hydrocarbons and hydrogen, and the hydrogen can be relatively diluted. A bottom stream 318 can include a condensed unstabilized gasoline and at least a portion provided to the first absorber 340, as hereinafter described, and typically another portion refluxed to a column in the fractionation zone 200. Optionally, a boot can be provided to remove any water from the receiver 310.

The separation zone 300 can include a gas recovery section based on an absorption system, but any suitable gas recovery system may be used, including a cold box system. To obtain sufficient separation of light gas components, the overhead stream 314 may be compressed in a compressor 330, which can use one or more compressor stages, such as a dual stage compression. Generally, the compressor 330 controls the pressure in downstream zones and equipment, such as the reaction vessel 500. A compressed stream 334 may be joined by streams 344 and 362, as hereinafter described, cooled, and provided to a second receiver 320. A bottom stream 328 can be sent to another separation zone 360, as hereinafter described. An overhead stream 324 including one or more gases, including dilute hydrogen and ethene, may be routed to a first absorber 340. In the first absorber 340, the gases in the overhead stream 324 may be contacted with the bottom stream 318 from the first receiver 310 including an unstabilized gasoline. This contacting may effect at least a partial separation between $C3^+$ and $C2^-$ hydrocarbons. A bottom stream 344 including one or more liquid $C3^+$ hydrocarbons can be combined with streams 334 and 362 before cooling and transferring to the second receiver 320. An overhead stream 342, including a primary off-gas, may include dilute hydrogen and ethene optionally with varying impurities such as hydrogen sulfide and ammonia. Thus, at least a portion of the light naphtha stream 210 may be processed by separating and compressing to obtain the overhead stream 342. In one preferred embodiment, this dilute hydrogen stream 342 can directed to a secondary absorber 350. A first portion 232 of the LCO stream 230 may be diverted and used to contact counter-currently the gases in the dilute hydrogen stream 342.

The light cycle oil may absorb at least some or a substantial part of any remaining one or more C3+ hydrocarbons. A bottom stream 354 including a light cycle oil that can be rich in one or more C3+ hydrocarbons may be returned to the fractionation zone 200. An overhead stream 352 of the secondary adsorber 350, including a diluted hydrogen, can include an FCC dry gas of predominantly one or more C2− hydrocarbons, including ethene.

Typically, the dilute hydrogen stream 352 can include about 1-about 25%, by weight, hydrogen, about 1-about 25%, by weight, nitrogen, about 25-about 55%, by weight, methane, about 5-about 45%, by weight, ethane, about 5-about 50%, by weight, ethene, and no more than about 5%, by weight, of one or more C3+ hydrocarbons including no more than about 0.5%, by weight, propene, based on the weight of the dilute hydrogen stream 352. Impurities in the dilute hydrogen stream 352 can include hydrogen sulfide, ammonia, one or more carbon oxides, such as carbon monoxide, and saturation levels of water.

The dilute hydrocarbon stream 352 can be sent to a treatment zone 400 to remove hydrogen sulfide, ammonia, and carbon monoxide and can include, optionally and independently, a first removal zone 420, a washing zone 430, and a second removal zone 440. Many impurities in a dry gas stream can poison an alkylation and a hydrogenation catalyst. Carbon monoxide can adsorb on metal sites, reducing activity. Ammonia can attack acid sites on the catalyst. Hydrogen sulfide may adversely impact metal functions on a catalyst. Acetylene can polymerize and gum the catalyst or equipment.

The first removal zone 420 can receive the dilute hydrogen stream 352 and may have an optional amine absorber unit to remove hydrogen sulfide to a lower concentration. Such a vessel may include trays and other contacting devices to enhance the interaction of the amine solvent and gases. Typically, the dilute hydrogen stream 352 has a hydrogen sulfide concentration of no more than about 1,000 ppm, by weight, based on the weight of the dilute hydrogen stream 352 that can be reduced, after absorption, to a hydrogen sulfide concentration of no more than about 50 ppm, by weight, based on the weight of the outlet stream 422. A lean aqueous amine solution, including, e.g., monoethanol amine or diethanol amine, may be introduced and contacted with the gases to adsorb hydrogen sulfide. Subsequently, a rich aqueous amine absorption solution containing hydrogen sulfide may be removed from the first removal zone 420.

Optionally, the outlet stream 422 can be provided to the washing zone 430 to remove residual amine carried over from the first removal zone 420 and reduce the concentration of ammonia and carbon dioxide of the dilute hydrogen stream 422. Water, optionally slightly acidified, may be introduced into a water wash vessel to enhance capture of basic molecules, such as the amine. Such a vessel may include trays and other contacting devices to enhance the interaction of the water and gases. An aqueous stream containing one or more amines, and potentially ammonia and carbon dioxide can leave the washing zone 430. Typically, the outlet stream 422 has an ammonia concentration of about 1,000 ppm, by weight, based on the weight of the stream 422 entering the washing zone 430 and can exit as an outlet stream 432 having an ammonia concentration of about 50 ppm, by weight, based on the weight of the outlet stream 432.

In one preferred embodiment, the outlet stream 432 can be provided to the second removal zone 440. The second removal zone 440 can include a guard bed to remove one or more of the impurities such as carbon monoxide, hydrogen sulfide and ammonia down to lower concentrations, but primarily reduce carbon monoxide. The guard bed may contain an adsorbent to adsorb impurities such as hydrogen sulfide that may poison a catalyst, or multiple adsorbents for adsorbing more than one type of impurity. Such adsorbents are commercially available from, e.g. UOP LLC of Des Plaines, Ill. The adsorbents may be mixed in a single bed or can be arranged in successive beds. In one exemplary embodiment, the stream 432 prior to entering the guard bed 440 can include no more than about 2%, by weight, or about 1%, by weight, carbon monoxide, based on the weight of the stream 432. After exiting the second removal zone 440, an outlet stream 442 or hydrogen stream 442 can have no more than about 100 ppm, by weight, carbon monoxide based on the weight of the stream 442. This hydrogen stream 442, typically having a dilute concentration of hydrogen, can be provided to the reaction vessel 500 after combination with other streams, as hereinafter described. Thus, the hydrogen stream 442 after passing through the treatment zone 400 can include no more than about 50 ppm, by weight, hydrogen sulfide, no more than about 50 ppm, by weight, ammonia, and optionally no more than about 100 ppm, by weight, carbon monoxide, based on the weight of the hydrogen stream 442. Although these impurities have been discussed, it should be understood that other impurities, such as water and/or acetylene, can also be removed.

Another fractionation zone 360 can receive the bottom stream 328 from the second receiver 320. The another fractionation zone 360 can include one or more columns. In one exemplary zone these one or more columns can include a stripper, a debutanizer column, and/or a naphtha splitter. The another fractionation zone 360 can provide a stream 362 including one or more C2− hydrocarbons and other gases typically from a stripper that can be combined with the streams 334 and 344 prior to cooling and passing to the receiver 320. Moreover, the fractionation zone 360 can provide a stream 364 including one or more C3-C4 alkenes, typically from an overhead stream of a debutanizer column. Additionally, the fractionation zone 360 can provide a stream 366 including one or more C5-C6 alkenes, typically from an overhead stream of a naphtha splitter. The streams 364 and 366 can, optionally and independently, be combined with the dilute stream 442. Furthermore, the naphtha splitter may provide a bottom stream 368 including a stabilized gasoline that may be further treated and sent to gasoline storage and blending.

The reaction vessel 500 can include an alkylation zone 520 and a hydrogenation zone 540 and receive a feed 490. The feed 490 can include one or more of the streams 442, 364, 366, and 394. The stream 394 can be a make-up hydrogen stream to supplement any missing hydrogen to increase the partial pressure of hydrogen. Thus, the streams 442 and 394 can comprise a combined hydrogen stream 396. The feeding of the stream 442, which can contain hydrogen and one or more alkenes, to the reaction vessel 500 can result in formation of single ring aromatics with additional alkyl functional groups and saturation of aromatic rings when combined with a second portion 234 of the LCO stream 230. Moreover, if the stream 442 has sufficient quantities of ethene, the addition of the streams 364 and 366 can be omitted. The reaction vessel 500 may be a fluidized bed reactor, moving bed reactor, fixed bed reactor or other known reactor type. In this exemplary embodiment, as depicted, it can be a fixed bed reactor.

In yet a further embodiment, at least one of the streams 364 and 366 can be introduced at the inlet of the reaction vessel 500 with the LCO to contact the catalyst with acid function, while at least a portion of the streams 442, 394, 364, and 366 can be introduced to the hydrogenation zone 540.

The alkylation zone 520 can include any suitable catalyst, such as at least one of zeolite from the FAU, MFI or ZSM-5, *BEA or beta zeolite, and MWW structure types, or an UZM-8 zeolite. Desirably, the catalyst has acidic components to facilitate alkylation. The LCO can contain a significant quantity of 2-ring aromatic and appreciable amounts of 3-ring aromatic and 1-ring aromatic compounds. Generally, the acidic and hydrogenation components of the catalyst can reside in separate particles.

The hydrogenation zone 540 can include any suitable catalyst, such as a catalyst containing a metal from groups 5-6, and 8-10 of the periodic table, such as a metal of vanadium, chromium, molybdenum, tungsten, nickel, palladium, and platinum. The metal can be deposited on any suitable support, such as a zeolite or an alumina. Although these catalysts have been disclosed for the zones 520 and 540, any suitable catalyst for the alkylation and hydrogenation of the aromatic and naphthenoaromatic molecules present in the LCO may be used.

Although not wanting to be bound by theory, the acidic particle can contact the feed 490 first to alkylate the aromatic ring, and the alkylation product can contact a second catalyst carrying the hydrogenation components to saturate one or more of the multi-aromatic rings. The overall effect is to produce a product stream with increased numbers of alkyl functional groups, and higher cetane number in comparison with LCO feed entering the reaction vessel 500.

One advantage of catalyst particles having separate acidic and hydrogenation functions can be allowing the alkylation and saturation reactions to take place under more optimal process conditions for the respective reactions. In addition, the saturation of the aromatic ring can take place afterwards to avoid saturating the olefin feed components designed to alkylate the aromatic ring. The alkylation zone 520 and the hydrogenation zone 540 can operate, independently, at a temperature of about 100-about 400° C., a pressure of about 790 kPa-about 7,000 kPa, preferably 1,500-about 7,000 kPa, and a space velocity of about 0.1-about 10 hr$^{-1}$. In addition, the alkylation zone 520 and the hydrogenation zone 540 can operate in a trickle bed or a gas phase operation.

In another exemplary embodiment, the zones 520 and 540 can contain the same catalyst possessing both alkylation and hydrogenation functions. In such an instance, conditions can be tailored, such as low hydrogen partial pressure, so the rate of alkylation exceeds the rate of hydrogenation so mostly alkylation occurs in the zone 520. Raising the hydrogen partial pressure can ensure that mostly hydrogenation, or alkylation and hydrogenation, occurs in the zone 540. In a still further exemplary embodiment, the zones 520 and 540 can be combined into a single zone with mostly alkylation occurring in the first part of the zone and mostly hydrogenation, or alkylation and hydrogenation, occurring in the second part of the zone.

The reaction vessel 500 can produce an alkylated and hydrogenated product stream 550. In one exemplary embodiment, the product steam 550 may be sent to a stripper for removing most of the light gases such as unreacted hydrogen, methane, ethane, unreacted olefins and light impurities. These light gases can be utilized as a typical fuel gas to generate steam or power. A liquid bottoms stream from the stripper can be sent to a diesel fuel pool for use as an improved diesel fuel or LCO blending stock. Alternatively, a portion of the liquid bottoms stream can be recycled back to the reaction vessel 500 for further upgrading.

Figure 2:
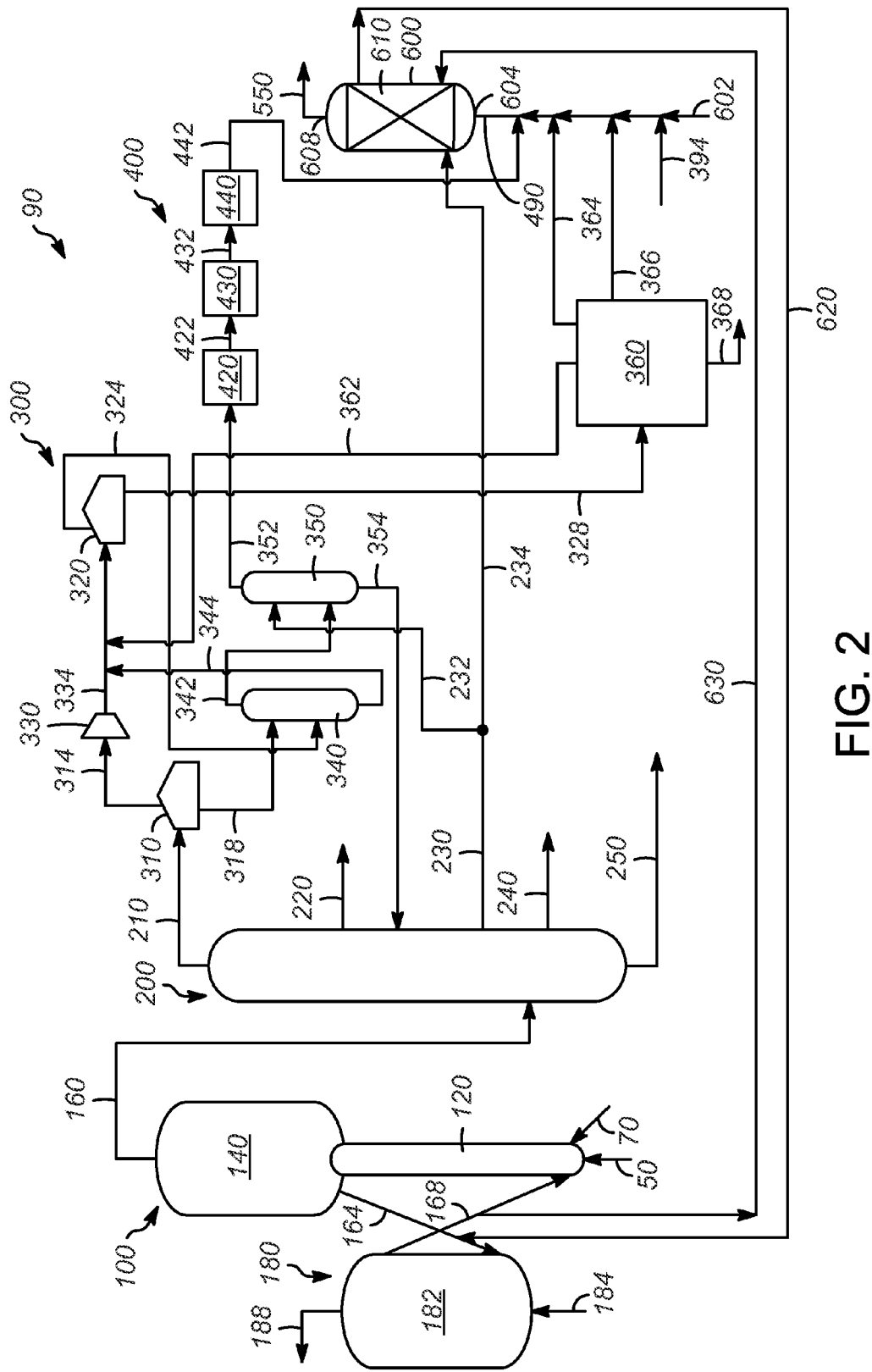
FIG. 2 is a schematic depiction of another version of an exemplary apparatus for alkylating and hydrogenating an LCO.

Referring to FIG. 2, another version of the apparatus 90 is disclosed. In this version, the reaction vessel 500 can be replaced with a reaction vessel 600, which may be a fluidized bed reactor operating in an upflow operation, and can contain at least one reaction zone 610. Generally, the utilized catalyst can be the same as the catalytic cracking zone 100, as described above. Particularly, the feed 490 can include streams 442, 364, 366, and 394. However, a fresh catalyst can be provided by a line 602 and combined with the feed 490. The hydrogen and alkene feed 490 can enter an inlet 604 to alkylate and hydrogenate the LCO 234, which can be provided proximate to the inlet 604, as well. The LCO may be alkylated and hydrogenated in contact with the feed 490 and the catalyst from a line 630 rising in the reaction vessel 600. The alkylated and hydrogenated product stream 550 can exit, and be sent to a stripper, as described above.

Spent or partially spent catalyst can be withdrawn from the reaction vessel 600 proximate to the outlet 608 and routed via a line 620 to the line 164, where the catalyst can be sent to the regeneration zone 180. Afterwards, the catalyst can be regenerated, and a portion removed from the line 168 and provided to the reaction vessel 600 via the line 630.

Generally, the embodiments disclosed herein can provide an improved fuel quality such as increased cetane numbers, lowered sulfur contents, and reduced end points for the LCO. Moreover, the LCO may have an increased alkyl functional group and 1-ring aromatic compounds in comparison with LCO feed entering the reaction vessel. Consequently, an increased proportion of the LCO can be blended in the diesel pool.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for alkylating and hydrogenating a light cycle oil, comprising:
   A) passing one or more C2-C6 alkenes, hydrogen, and the light cycle oil upwards through a reaction vessel containing a reaction zone for alkylating and hydrogenating the light cycle oil; and
   B) sending a catalyst from the reaction zone to a regeneration zone in a catalytic cracking zone.

2. The process according to claim 1, wherein the catalyst comprises a first component comprising a FAU zeolite and a second component comprising an MFI zeolite.

3. The process according to claim 2, wherein the catalyst further comprises at least one of nickel and vanadium.

4. The process according to claim 1, further comprising providing a regenerated catalyst proximate to an inlet of the reaction vessel and withdrawing a spent catalyst proximate to an outlet of the reaction vessel.

5. The process according to claim 1, wherein the catalytic cracking zone comprises a fluid catalytic cracking zone.

6. The process according to claim 5, wherein the hydrogen is at least partially comprised from a hydrocarbon product stream from the fluid catalytic cracking zone.

7. The process according to claim 6, further comprising fractionating and separating the hydrocarbon product stream to obtain a stream comprising hydrogen and ethene.

\* \* \* \* \*